US009408987B2

(12) United States Patent
Hearn et al.

(10) Patent No.: US 9,408,987 B2
(45) Date of Patent: Aug. 9, 2016

(54) INHALER

(75) Inventors: Alex Hearn, London (GB); Iain McDerment, Royston (GB)

(73) Assignee: Kind Consumer Limited, London (GB)

( * ) Notice: Subject to any disclaimer, the term of this patent is extended or adjusted under 35 U.S.C. 154(b) by 953 days.

(21) Appl. No.: 13/389,434

(22) PCT Filed: Aug. 6, 2010

(86) PCT No.: PCT/GB2010/001487
§ 371 (c)(1),
(2), (4) Date: Feb. 7, 2012

(87) PCT Pub. No.: WO2011/015825
PCT Pub. Date: Feb. 10, 2011

(65) Prior Publication Data

US 2012/0138052 A1 Jun. 7, 2012

(30) Foreign Application Priority Data

Aug. 7, 2009 (GB) .................................. 0913942.9
Jan. 11, 2010 (GB) .................................. 1000403.4
Feb. 8, 2010 (GB) .................................. 1002024.6

(51) Int. Cl.
*A61M 15/06* (2006.01)
*A61M 15/00* (2006.01)
(Continued)

(52) U.S. Cl.
CPC .......... *A61M 15/0091* (2013.01); *A24F 47/002* (2013.01); *A61M 15/0093* (2014.02); *A61M 15/06* (2013.01); *A61M 16/20* (2013.01); *A61M 2205/8225* (2013.01)

(58) Field of Classification Search
CPC .................... A61M 15/0091; A61M 15/0093; A61M 15/06; A61M 16/20; A61M 2205/8225; A24F 47/002
USPC ............ 128/202.21, 200.21, 203.12, 203.23, 128/203.16, 203.17; 131/273, 194, 271, 131/329, 330, 360
See application file for complete search history.

(56) References Cited

U.S. PATENT DOCUMENTS 3,631,856 A 1/1972 Taylor
4,393,884 A 7/1983 Jacobs
(Continued)

FOREIGN PATENT DOCUMENTS

FR 1601834 A 9/1970
WO 0245783 A1 6/2002
(Continued)

OTHER PUBLICATIONS

International search report for application No. PCT/GB2010/001487 dated Nov. 23, 2010.
(Continued)

*Primary Examiner* — Tan-Uyen (Jackie) T Ho
*Assistant Examiner* — Mark Wardas
(74) *Attorney, Agent, or Firm* — Patterson & Sheridan, LLP

(57) ABSTRACT

An inhaler comprising a reservoir of an inhalable composition with an outlet at one end through which the inhalable composition is discharged. A non-metered breath-activated valve is provided between the one end and the reservoir, the breath-activated valve comprising a flow path extending from the reservoir to the outlet end. At least a portion of the flow path is a deformable tube. A clamping member pinches the deformable tube closed when no suction force is applied to the device and releases the tube to open the flow path when suction is applied at the outlet, to provide uninterrupted flow from the reservoir to the outlet.

13 Claims, 6 Drawing Sheets

(51) Int. Cl.

| | |
|---|---|
| ***A24F 47/00*** | (2006.01) |
| ***A61M 16/20*** | (2006.01) |
| *A61M 16/00* | (2006.01) |

(56) References Cited

U.S. PATENT DOCUMENTS 4,945,929 A * 8/1990 Egilmex .......................... 131/273
4,945,931 A 8/1990 Gori
5,027,808 A 7/1991 Rich et al.
5,598,840 A 2/1997 Iund et al.
6,581,590 B1 6/2003 Genova et al.
6,629,528 B1 10/2003 Wickham et al.
6,889,687 B1 5/2005 Olsson
7,225,805 B2 * 6/2007 Bacon ...................... 128/200.23
2002/0018181 A1 * 2/2002 Manne .................... A61L 9/122 352/85
2003/0010946 A1 1/2003 Furukawa et al.
2004/0118396 A1 6/2004 Hughes et al.
2005/0010996 A1 * 1/2005 Steinert ............................. 2/458
2008/0142008 A1 6/2008 Pocock et al.
2011/0315152 A1 * 12/2011 Hearn et al. .................. 131/273

FOREIGN PATENT DOCUMENTS

WO 2008/049433 A1 5/2008
WO 2008130813 A1 10/2008
WO 2009001078 A2 12/2008
WO 2009001082 A1 12/2008

OTHER PUBLICATIONS

GB examination report for application No. GB1106397.1 dated May 19, 2011.
GB search report for application No. GB0913942.9 dated Mar. 31, 2010.

* cited by examiner

INHALER

The present invention relates to an inhaler.

The invention has been specifically designed for a simulated cigarette device having a generally cigarette-shaped body. However, the invention relates to a development of the outlet valve for such a device which has broader applications in the field of inhalers, for example, medicinal inhalers for oral drug delivery such as asthma inhalers.

In the field of cigarette replacements, there have been a number of proposals to create a simulated cigarette. Such a device has a number of advantages over traditional nicotine replacement therapies such as patches and gum in that they recreate the physical act of smoking which is psychologically important to a smoker, and also are able to deliver nicotine as a dose which more closely replicates the pharmacokinetic effects of a cigarette that persistent smokers desire. Thus, a smoker is able to obtain the "hit" that is familiar from a cigarette, rather than having to deal with the slow release from a patch or gum which does not produce such a hit which leads to unpredictable dosings and poor craving scores and cessation rates.

A simulated cigarette has a reservoir of inhalable composition and an outlet valve which can be triggered, for example, by pushing a button or biting on the end of a cigarette. However, a preferred mechanism for opening the valve is to provide a breath-activated valve as this ensures that the cigarette will only dispense when the user sucks on the device in a manner of a normal cigarette.

WO 02/45783 discloses a drug dispenser having a valve arrangement suitable for dispensing a metered dose. This takes the form of a flexible tube which is wrapped around a valve element and has a pair of kinks. The portion of the tube between the kinks is able to retain a metered dose of the drug to be dispensed. When a user sucks on the dispenser, the valve element moves opening the downstream kink in order to dispense the metered dose. On exhalation, the valve moves in the opposite direction closing the downstream kink and opening the upstream kink to allow the portion of the tube between the kinks to be re-charged with the drug. This arrangement only ever allows a user to inhale one metered dose no matter how long they suck on the device.

U.S. Pat. No. 4,393,884 discloses one such device which has a large resilient "tongue" with a flow path passing through it. This tongue is biased into a first position in which it is out of alignment with the outlet of the cigarette and can be sucked into a second position in which it aligns with the outlet of the cigarette to provide a flow path from the reservoir to the outlet. Such a device is difficult to seal in the first position. It will also require considerable force in order to suck the tongue to the open position against the action of a retaining spring and the relatively large mass of the tongue means that it will be difficult to return to the closed position meaning that dispensing will continue after the suction has been removed.

U.S. Pat. No. 6,889,687 discloses a further example of a simulated cigarette with a breath-activated valve. This discloses a number of examples. One of these has a pair of magnets, one of which is retained by a flexible membrane which allows the magnet to moved apart when suction is applied to a device. This opens up a flow path from the reservoir. However, the mechanism is reasonably complex, has a tortuous flow path which is likely to impede delivery of the composition from the reservoir, and is "binary" in nature in the sense that the valve is either open or closed. It does not provide the ability for the user to regulate the amount of flow by varying the degree of suction. A second example is a spring-biased plunger which is moved axially to open up a passageway in a central rod. Such an axially movable plunger is undesirable in practice as it has been found that the level of suction required to overcome the spring biasing force is too high to be usable in practice. Also, the flow path in the open position is out of the rod, into the plunger and back into the rod so that it is again somewhat tortuous. The third example relies on a magnetic interface where the force on which is overcome by a system of vanes which rotate about the axis of the device, thereby moving along a cam surface to pull the magnetic valve element from its seat. Again, this suffers from problems of complexity, lack of control and a tortuous flow path.

WO 2009/001082 which is our own earlier application discloses two different breath-activated devices. The first of these has a pair of vane systems rotatable about an axis perpendicular to the main axis of the device to align an orifice with the outlet orifice from the reservoir enabling dispensing. The second of these has a pair of hinged flaps which are sucked down against the action of return springs in order to open the flow path. While this solves some of the problems in that it provides a simple mechanism and an axial flow path, the force required as suction to trigger the device is comparatively large and the user, as a result, can exert less control over the system to release a variable dose, small or large according to the inhalation intake.

The present invention is aimed at providing an improved breath-operated valve for an inhaler and, particularly, a simulated cigarette.

According to the present invention, there is provided an inhaler comprising:

a reservoir of an inhalable composition;

an outlet at one end through which the inhalable composition is discharged; and a non-metered breath-activated valve between the one end and the reservoir, the breath-activated valve comprising a flow path extending from the reservoir to the outlet end, at least a portion of the flow path being a deformable tube, and a clamping member which pinches the deformable tube closed when no suction force is applied to the device and releases the tube to open the flow path when suction is applied at the outlet, to provide uninterrupted flow from the reservoir to the outlet.

By clamping a deformable tube, the present invention has a number of advantages. The clamping mechanism is simple as all that is required is a movable component to pinch the tube which need not be complex. Further, as the flow path is along an opened tube, there is no need for a tortuous flow which may otherwise be required to flow around an unseated valve component such as those in U.S. Pat. No. 6,889,687. The non-metered valve which allows uninterrupted flow allows a user to regulate the dose that they receive from the inhaler, as it will continue to dispense for as long as the user sucks.

The pinched tube arrangement lends itself well to an unmetered dosage. Also, while the device may be provided with the clamping member which effectively "snaps" open to provide a "binary" device which is either open or closed, the pinched deformable tube is well suited to a device in which the degree of opening of the tube is proportional to the strength of the suction. Such an outlet valve which is breath-operable and of varied resistance according to the inhalation profile it is actuated by, allows the user to self-titrate the inhaled dose in a continuous manner. This has applications firstly for smoking cessation inhaler devices where users want to self-titrate their dose of nicotine in a manner that fits their need, but also in other area such a pain management, diabetes, asthma and COPD where self-administered doses are preferable via the oral route.

The tube could be clamped at several locations but is preferably clamped at a single location as that is all that is necessary to fulfil its function. The flow path is preferably substantially straight to ensure a smooth flow.

As mentioned above, the inhaler may be a drug delivery inhaler for any inhalable pharmaceutical composition. However, the inhaler is preferably a simulated cigarette device having a generally cigarette-shaped body. In this case, the inhalable composition preferably includes nicotine or a nicotine derivative or salt thereof. On the other hand, it may be a simulated cigarette which replicates the physical act of smoking without requiring nicotine in the composition. Alternatively, the composition may include patient controlled analgesics, anti-inflammatory, bronchodilators, anti-spasmodics, retro-virals or opiates.

The clamping member may be formed of any suitable device which can release the deformable tube when suction is applied to the outlet. This could, for example, be a combination of an electronic flow sensor and a solenoid to move the clamping member. However, preferably, the clamping member is a mechanical member which is moved by a pressure differential caused when suction is applied at the outlet.

The mechanical member may take the form of the pair of vanes of the second example of WO 2009/001082 where it is pinched between the vanes in the closed position and is released as the vanes pivot towards the direction of the air through-flow.

However, preferably, the clamping member is an elongate vane which is pivotally mounted at one end and extends longitudinally within the inhaler, the vane being pivotable between a first position in which the tube is closed and a second position in which it releases the tube to provide the flow path. There may be a single vane which clamps the deformable tube against a fixed part of the inhaler, or there may be a pair of such vanes between which the tube is clamped.

Preferably, the or each vane is biased into the closed position and the inhaler has a second flow path creating a pressure differential across the vane which overcomes the biasing force.

The or each vane may be exposed to a through-flow of air such that, as a user sucks on the outlet, the through-flow of air impinges on an outer surface of the vane to move it inwardly. However, preferably, the or each vane is supported by a flexible membrane. This flexible membrane creates a chamber in which the vane is housed and which is open to the outlet, but is otherwise sealed, with the face of the membrane on the opposite side to the vane being open to atmospheric pressure. When a user sucks on the outlet, they create a negative pressure within the chamber to move the vane and the membrane flexes to allow this movement. This provides a very efficient mechanism for conveying the suction force to the vane.

Preferably, the deformable tube is a nozzle which is also provided integrally with an outlet orifice, which is the narrowest part of the flow path.

In this case, preferably the nozzle has an outwardly projecting annular flange at its upstream end which fits within a downstream end of the flow path.

Examples of inhalers in accordance with the present invention will now be described with reference to the accompanying drawings, in which.

The present invention relates to an improvement of the outlet valve for a breath-activated cigarette and only this aspect of the invention will be specifically described here. For details of the construction of the remainder of the cigarette device and its refill mechanism, reference is made to WO 2009/001078.

Figure 1:
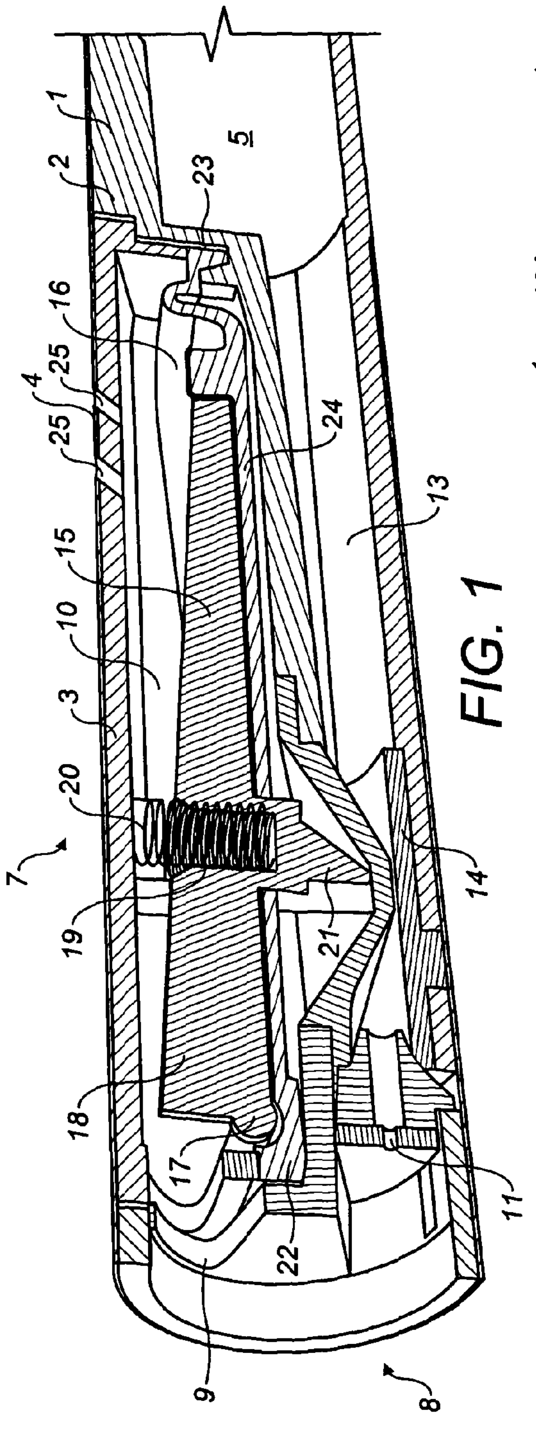
FIG. 1 is a section through a perspective view of a first inhaler in a closed position.
Figure 2:
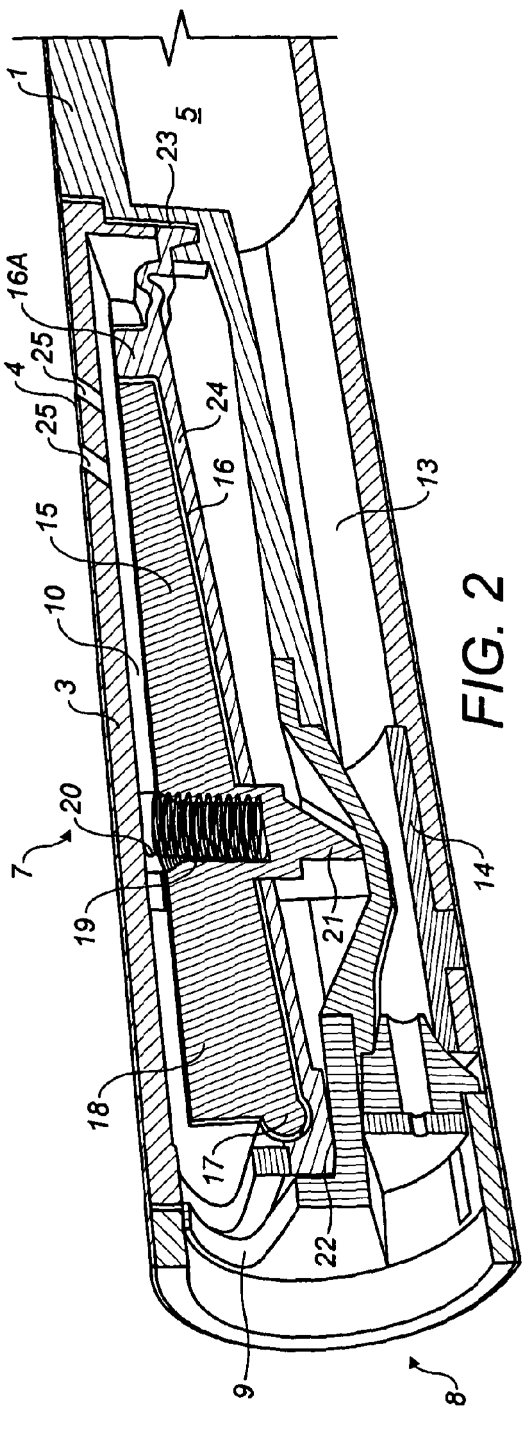
FIG. 2 is a similar view in the open position.
Figure 3:
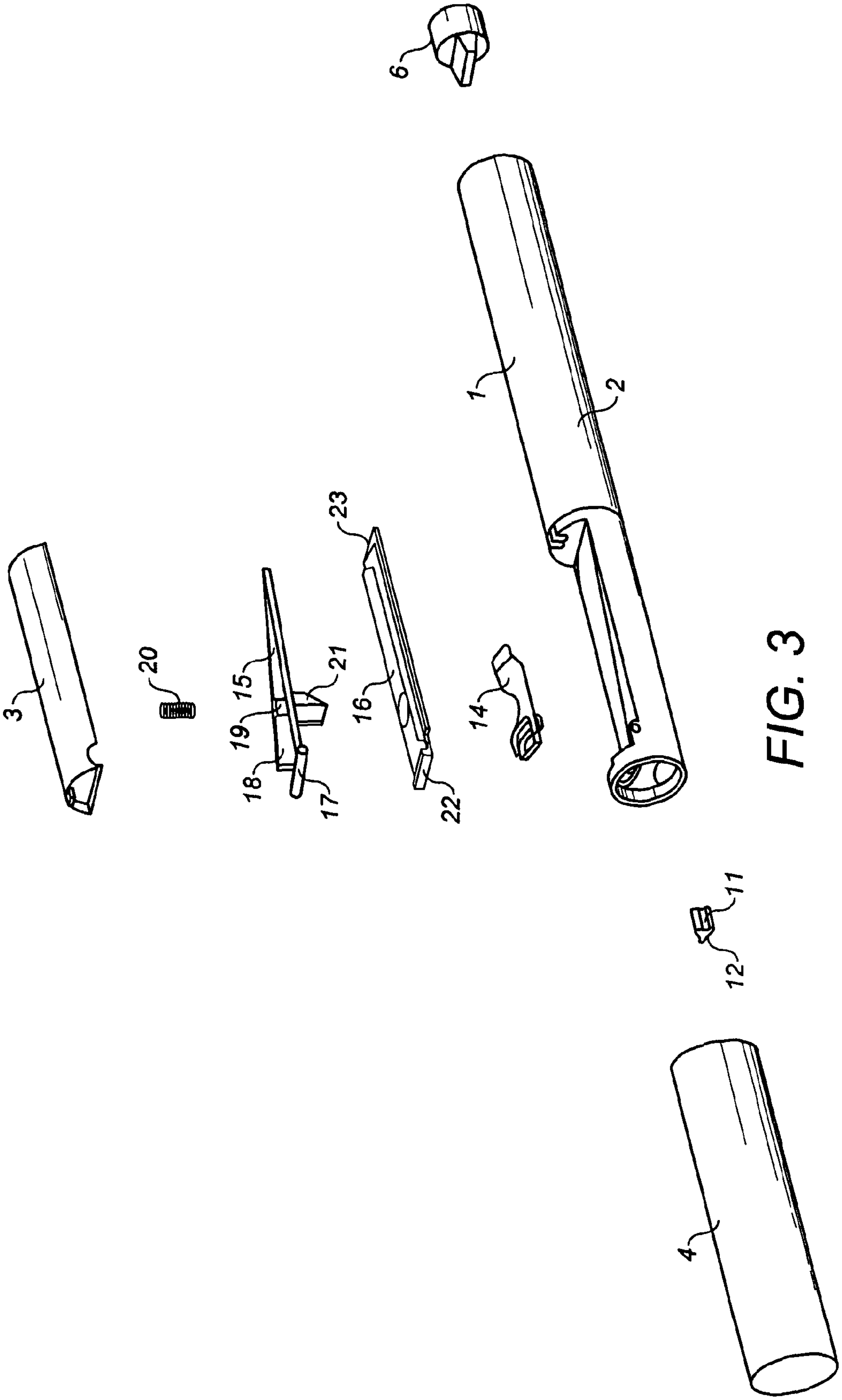
FIG. 3 is an exploded perspective view of the inhaler of FIGS. 1 and 2.

The first example of an inhaler in accordance with the present invention is shown in FIGS. 1 to 3.

The device has a housing 1 made up of a main chassis 2 and a closure element 3 as shown in FIG. 1. This is held in place by label 4. Within the housing, there is a reservoir 5 containing the inhalable composition. This is preferably pressurised but could also work with a non-pressurised reservoir in combination with a Venturi nozzle to generate an enhanced suction force on the reservoir, or a non-pressurised reservoir containing a substance that is prone to evaporating at room temperature. It may be refillable as described in WO 2009/001082 through the filling valve 6, or the device may be a single use device, or may be arranged so that the reservoir 5 is a replaceable component.

The breath-activated valve 7 is positioned between an outlet end 8 and the reservoir 5. The breath-activated valve is arranged so that, when a user sucks on the outlet end 8, the breath-activated valve 7 opens to allow the inhalable composition from the reservoir 5 to be inhaled.

The housing at the outlet end has two orifices. The first of these is the suction orifice 9 which communicates with a chamber 10 as will be described in greater detail below and the second is an outlet orifice 11 from which the inhalable composition dispensed is also described in more detail below. As is apparent from FIG. 3, the outlet orifice 11 is provided on a separate component 12.

An outlet path 13 is defined between the reservoir 5 and outlet orifice 11.

A portion of the outlet path 13 is provided by deformable tubular element 14. This tubular element is moved between the closed position shown in FIG. 1 and the open position shown in FIG. 2 by a mechanism which will now be described.

This mechanism comprises a pivotally mounted vane 15 and a membrane 16. The pivotally mounted vane has a pivot 17 at the end closest to the outlet end 8 and a central reinforcing rib 18 running along its length and tapering away from the outlet end. At around the midpoint, the vane 15 is provided with a recess 19 for receiving a spring 20 which biases it into the closed position shown in FIG. 1. Below the recess 19 is a jaw 21 having a triangular cross-section which is configured to apply the force provided from the vane 15 to the deformable tube 14 over a narrow area. The vane 15 is supported by the diaphragm 16 which is sealed to the housing at its ends 22, 23. This seals off the chamber 10 other than to the suction orifice 9.

The underside 24 of the membrane 16 is open to atmospheric pressure as a leakage path exists through the housing 1 which is not shown in the drawings as it extends around the outlet path 1 and is therefore not shown in the plane of FIGS. 1 and 2.

When a user sucks on the outlet end 8 with the device in the configuration shown in FIG. 1, the suction is communicated by the suction orifice 9 to the chamber 10 through orifices 25 thereby lowering the pressure in this chamber. This causes the vane 15 to be lifted against the action of the spring 20 to the position shown in FIG. 2 deforming the diaphragm into the configuration shown in FIG. 2 and lifting the jaw 21 to allow the deformable tube to open, thereby allowing the inhalable composition from the reservoir 5 along outlet path 13 through the deformable tube 14 and out through the outlet orifice 11. The degree of suction applied by the user will determine the extent to which the vane 15 moves and therefore the amount of composition that the user receives. As soon as a user stops sucking, atmospheric pressure will return to the chamber 10 via the suction orifice 9 and the spring 20 will return the vane to the FIG. 1 position thereby pinching the tube 14 closed.

Figure 4:
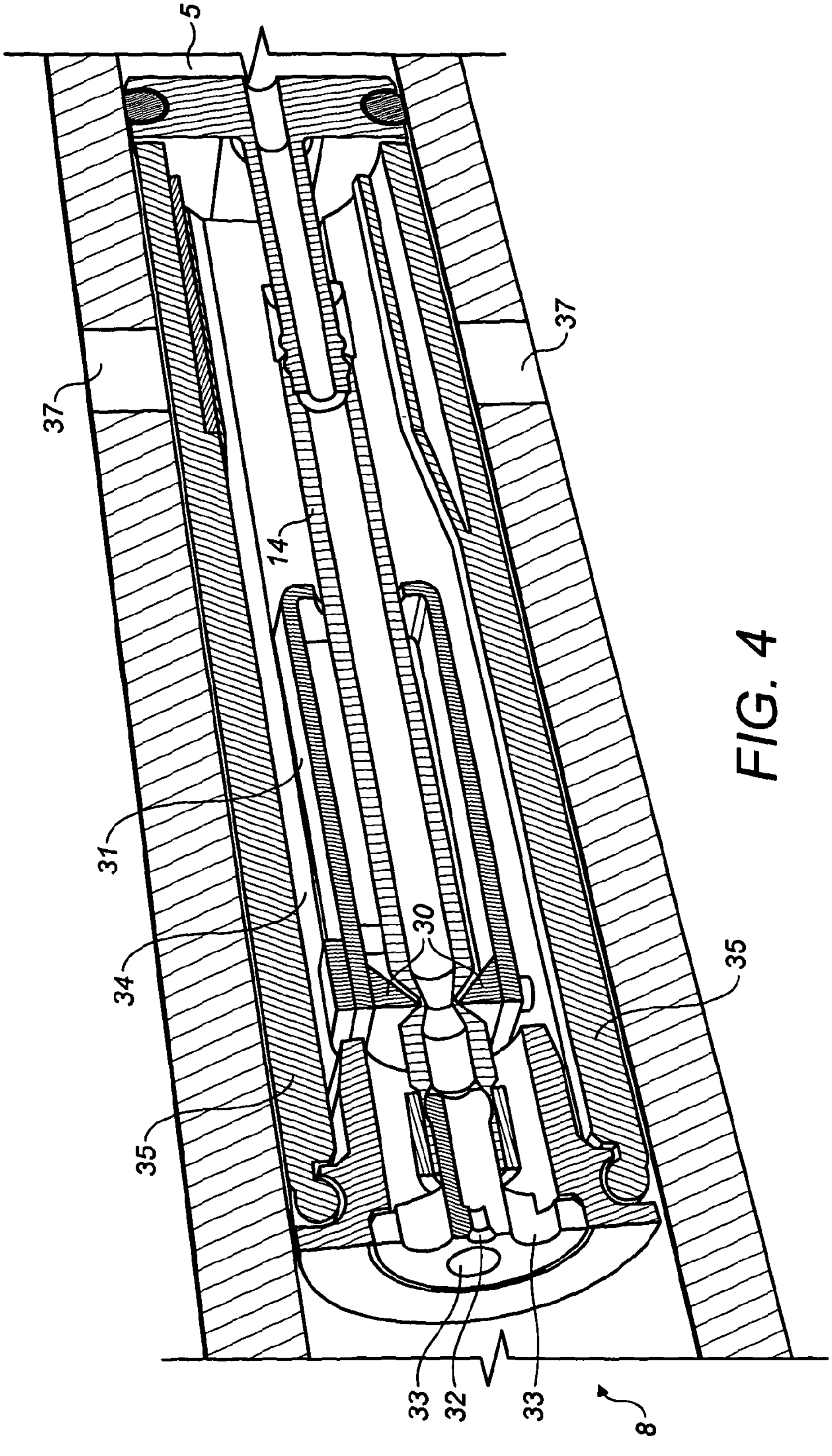
FIG. 4 is a cross-section through a perspective view of a second inhaler in the closed position.
Figure 5:
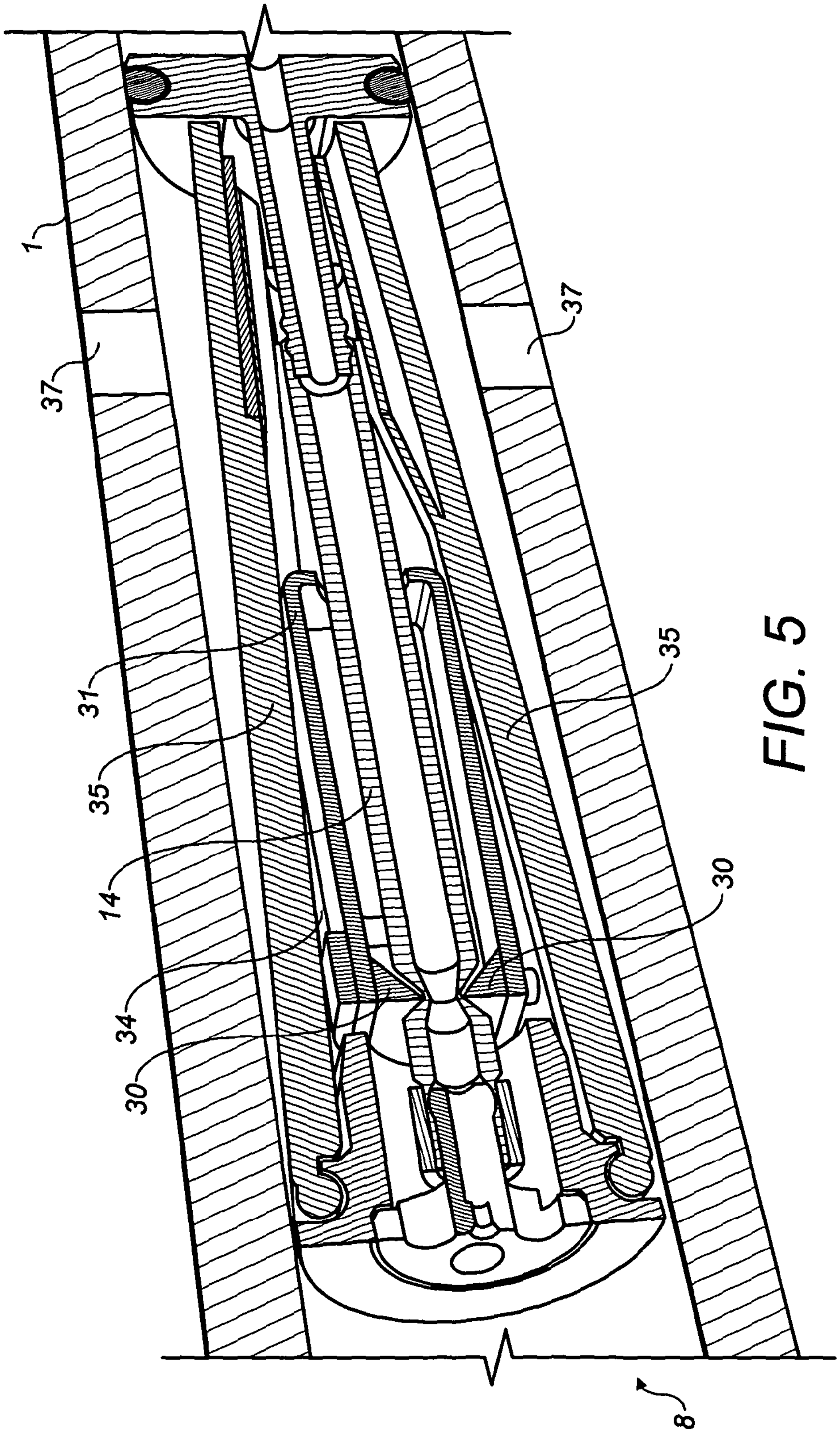
FIG. 5 is a similar view in the open position.
Figure 6:
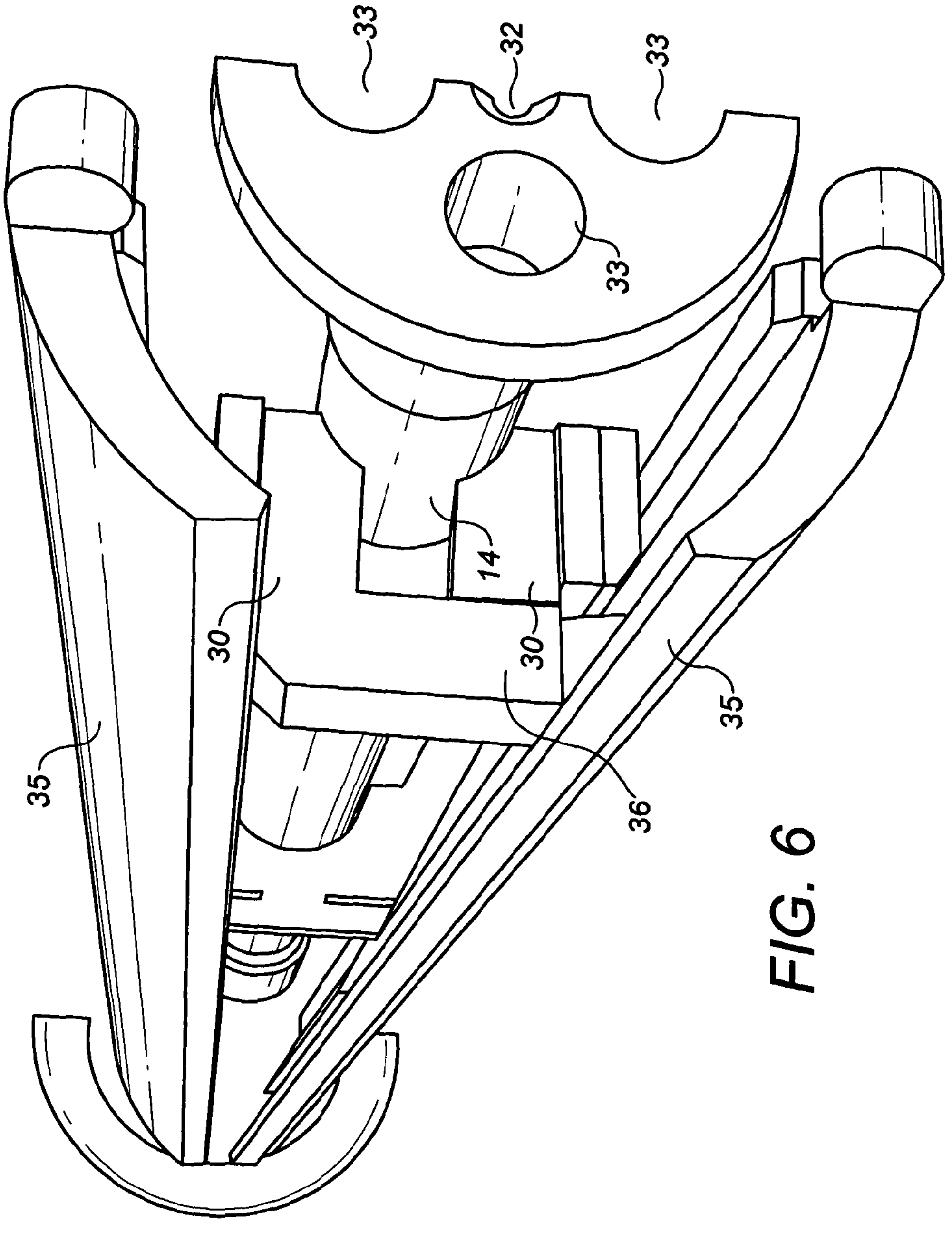
FIG. 6 is a perspective view from the outlet end of the second example shown with the outer housing removed to show the pinch mechanism.

A second example of an inhaler is shown in FIGS. 4 to 6. This is also provided with a deformable tube 14, a reservoir 5 and outlet end 8, but the mechanism is somewhat different. In the closed position of FIG. 4, the deformable tube is pinched between a pair of jaws 30 on a spring clip 31. This clip 31 is biased into the first position shown in FIG. 4. The inhaler has an outlet orifice 32 which completes a flow path from the reservoir 5 via the deformable tube 14 through the outlet orifice 32, and a plurality of suction orifices 33 which provide suction to an internal chamber 34. In this example, there are a pair of pivotally mounted vanes 35 extending longitudinally along opposite sides of the device. Each of the vanes is connected to an L-shaped bracket 36, one of which is shown in FIG. 6. This L-shaped bracket extends into the respective jaw 30 and effectively reaches around to the opposite side of the deformable tube 14 for reasons described below.

The housing 1 is provided with a pair of inlet orifices 37 one for each vane. As a user sucks on the outlet end 8, the suction force via suction orifices 34 draws air through inlet orifices 37 into chamber 34 thereby applying inward pressure to the vanes 35. As a result of inward pressure, the vanes pivot inwardly to the position shown in FIG. 5. The L-shaped brackets 36 mean that the downward movement of the upper vane 35 moves the lower jaw 30 downwardly and the upward movement of the lower vane 35 moves the upper jaw 30 downwardly, thereby opening the deformable tube 14 as shown in FIG. 5 to dispense the inhalable composition. When the suction force is removed, the pressure differential across the vanes 35 is removed and the resilience of the spring clip 31 returns the jaws 30 to the position shown in FIG. 4.

Figure 7:
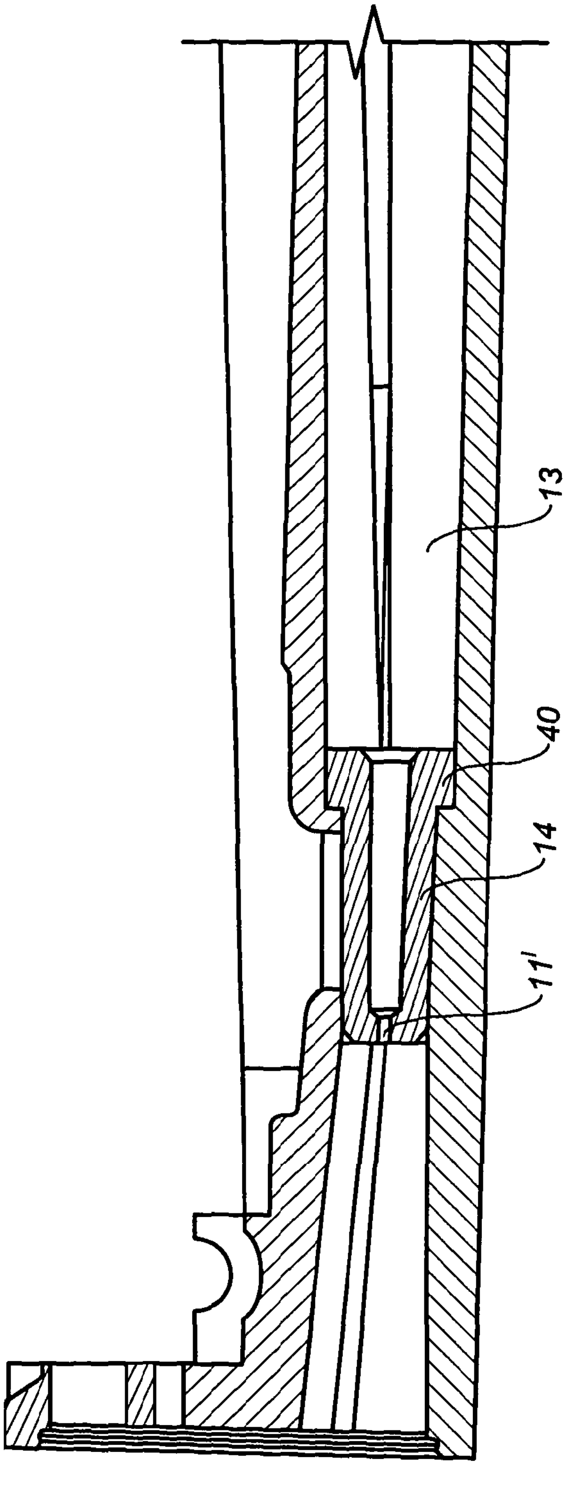
FIG. 7 is a cross-section of an alternative arrangement of deformable tubular element.

An alternative arrangement of a deformable tubular element will now be described with reference to FIG. 7.

The vane 15, membrane 16 and other components are broadly the same as those described with reference to the previous example. The main difference in this example is the configuration of the deformable tubular element 14' and these differences are all that will be described below.

Essentially, the orifice 11 which was previously in a separate component has now been integrated into the tubular element 14' as orifice 11'. This has some additional benefits. Firstly, by replacing the two components with a single component, the overall space required for the outlet path has been reduced. This allows other elements such as the vane 15 and membrane 16 to be increased in size. This, in turn, increases the sensitivity of the device as it is more efficient at converting small breath forces into a movement which opens the flow path. This is important for users who may have impaired lung function capacity. Secondly, by eliminating the requirement for a seal between the tubular element 14 and the plate with the orifice 11, the manufacturing of the device can be simplified. In addition, this eliminates the potential for leakage at this interface. Also, the manner in which the orifice plate 14' is sealed to the outlet path 13 at its upstream end has also been modified. At its upstream end, the tubular element 14' is provided with an outwardly projecting annular flange 40. This fits within the downstream end of the outlet path 13. This provides a more reliable sealing arrangement than bonding the tubular element 14 in place. As a result, the new nozzle design can contain a pressurised formulation without leakage for a much longer period, and thus increase the stability of the formulation within the device as well as retaining a higher capacity for a longer period.

The tubular element 14' can be different thicknesses at particular parts. For example, the hoop stresses will be greatest on the walls of the nozzle immediately downstream of the flange 40. However, for the mid-section of the tubular element 14' where the jaw 21 is sealing the tubular member, the material can be of reduced thickness to allow an easier clamping action.

Preferably, the tubular element 14' has a shore hardness of between 20A and 80A, most preferably 30A to 40A. At its thickest part, the wall can be 0.5 mm thick and at its thinnest part can be 0.18 mm thick. In order to deliver the optimum performance for the aerosol to reach the pulmonary system on inhalation, the outlet orifice 11 is preferably between 0.1 mm and 0.5 mm wide, but preferably 0.2 to 0.3 mm and most preferably 0.2 mm wide. The inner channel in the tubular element 14' away from the outlet orifice 11 is preferably between 0.2 mm and 0.6 mm wide, preferably between 0.3 mm and 0.5 mm and most preferably 0.4 mm.

The invention claimed is:

1. An inhaler comprising:

a reservoir of an inhalable composition;

an outlet at one end through which the inhalable composition is discharged;

a non-metered breath-activated valve between the one end and the reservoir, the breath-activated valve comprising a substantially straight flow path extending from the reservoir to the outlet end, at least a portion of the flow path being a deformable tube, and a clamping member which pinches the deformable tube closed when no suction force is applied to the inhaler and releases the tube to open the flow path when suction is applied at the outlet, to provide uninterrupted flow from the reservoir to the outlet.

2. An inhaler according to claim 1, wherein the clamping member is configured so that a degree of opening of the flow path is proportional to a strength of the suction.

3. An inhaler according to claim 1, wherein the clamping member is a mechanical member which is moved by a pressure differential caused when suction is applied at the outlet.

4. An inhaler according to claim 1, wherein the deformable tube is a nozzle which is also provided integrally with an outlet orifice, which is the narrowest part of the flow path.

5. An inhaler according to claim 4, wherein the nozzle has an outwardly projecting annular flange at an upstream end of the nozzle which fits within a downstream end of the flow path.

6. An inhaler according to claim 1, wherein the tube is clamped at a single location.

7. An inhaler comprising:

a housing having an inner wall and an outer wall;

a reservoir of an inhalable composition, the reservoir at least partially defined by the inner wall of the housing, the reservoir having a fixed orientation relative to the housing, wherein during use of the inhaler, there is no movement of the inner wall that defines the reservoir with respect to the outer wall of the housing at an end of the reservoir;

an outlet at one end through which the inhalable composition is discharged; and a non-metered breath-activated valve between the one end and the reservoir, the breath-activated valve comprising a flow path extending from the reservoir to the outlet end, at least a portion of the flow path being a deformable tube, and a clamping member which pinches the deformable tube closed when no suction force is applied to the inhaler and releases the tube to open the flow path when suction is applied at the outlet, to provide uninterrupted flow from the reservoir to the outlet.

8. An inhaler according to claim 7, wherein the clamping member is configured so that a degree of opening of the flow path is proportional to a strength of the suction.

9. An inhaler according to claim 7, wherein the clamping member is a mechanical member which is moved by a pressure differential caused when suction is applied at the outlet.

10. An inhaler according to claim 7, wherein the deformable tube is a nozzle which is also provided integrally with an outlet orifice, which is the narrowest part of the flow path.

11. An inhaler according to claim 10, wherein the nozzle has an outwardly projecting annular flange at an upstream end of the nozzle which fits within a downstream end of the flow path.

12. An inhaler according to claim 7, wherein the flow path is substantially straight.

13. An inhaler according to claim 7, wherein the tube is clamped at a single location.

* * * * *